United States Patent
Bigg et al.

(10) Patent No.: US 8,624,037 B2
(45) Date of Patent: Jan. 7, 2014

(54) IMIDAZOLIDINE-2,4-DIONE DERIVATIVES AND USE THEREOF AS A MEDICAMENT

(75) Inventors: Dennis Bigg, Gif sur Yvette (FR); Serge Auvin, Palaiseau (FR); Christophe Lanco, Dourdan (FR); Grégoire Prevost, Antony (FR)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 0 days.

(21) Appl. No.: 13/264,972

(22) PCT Filed: Apr. 16, 2010

(86) PCT No.: PCT/FR2010/000316
§ 371 (c)(1),
(2), (4) Date: Dec. 22, 2011

(87) PCT Pub. No.: WO2010/119194
PCT Pub. Date: Oct. 21, 2010

(65) Prior Publication Data
US 2012/0095068 A1    Apr. 19, 2012

(30) Foreign Application Priority Data
Apr. 17, 2009 (FR) ...................... 09 01864

(51) Int. Cl.
*A61K 31/4166* (2006.01)
*C07D 403/06* (2006.01)
*C07D 403/12* (2006.01)

(52) U.S. Cl.
USPC ............... 548/314.1; 548/311.1; 514/391

(58) Field of Classification Search
USPC ................. 548/311.1, 314.1; 514/391
See application file for complete search history.

(56) References Cited

U.S. PATENT DOCUMENTS 3,684,774 A * 8/1972 Merten et al. ............ 548/314.1
3,903,053 A * 9/1975 Iwata et al. .................. 528/353

FOREIGN PATENT DOCUMENTS

WO    WO 2008/017381    2/2008

OTHER PUBLICATIONS

International Preliminary Examination Report for International Application No. PCT/EP2007/006594, mailed Oct. 18, 2011.

* cited by examiner

*Primary Examiner* — Yong Chu
*Assistant Examiner* — Sonya Wright
(74) *Attorney, Agent, or Firm* — Hunton & Williams LLP (57) ABSTRACT

The subject matter of the present application is novel imidazolidine-2,4-dione derivatives. These products have an antiproliferative activity. They are particularly advantageous for treating pathological conditions and diseases associated with abnormal cell proliferation, such as cancers. The invention also relates to pharmaceutical compositions containing said products and to the use thereof for preparing a medicament.

23 Claims, 3 Drawing Sheets

IMIDAZOLIDINE-2,4-DIONE DERIVATIVES AND USE THEREOF AS A MEDICAMENT

This application is a national stage of filing of PCT/FR2010/000316, filed Apr. 16, 2010, the subject matter of which is incorporated herein in its entirety. This application further claims priority to FR 0901864, filed Apr. 17, 2009, the subject matter of which is incorporated herein in its entirety.

FIELD OF THE INVENTION

A subject of the present application is novel imidazolidine-2,4-dione derivatives. These products have an anti-proliferative activity. They are particularly useful for treating the pathological states and the diseases linked to an abnormal cell proliferation such as cancers. The invention also relates to the pharmaceutical compositions containing said products and their use for the preparation of a medicament.

STATE OF THE ART

Detailed Description of the Invention

Nowadays, cancer still constitutes one of the major causes of death despite there being numerous molecules on the medicament market.

It is therefore necessary to identify more powerful novel molecules allowing a better anti-tumour response, specifically by a good inhibitory activity on the proliferation of tumour cell colonies.

Such molecules are therefore particularly useful for treating the pathological states linked to an abnormal cell proliferation. They can therefore be used for the treatment of tumours or cancers, for example, those of the oesophagus, the stomach, the intestines, the rectum, the oral cavity, the pharynx, the larynx, the lung, the colon, the breast, the cervix uteri, the corpus endometrium, the ovaries, the prostate, the testes, the bladder, the kidneys, the liver, the pancreas, the bones, the connective tissues, the skin such as melanomas, the eyes, the brain and the central nervous system, as well as cancer of the thyroid gland, leukaemia, Hodgkin's disease, non-Hodgkin's lymphomas, multiple myelomas and other cancers.

It is of particular interest to find therapies for hormone-dependent cancers, for tumours expressing androgen receptors, for cancers of the breast and prostate.

The use of the anti-androgens in prostate cancer is based on their property of entering into competition with the natural agonists of the androgen receptor. However, the efficacy of these anti-androgens appears to be limited over time, in the end treatments are failing patients. Several hypotheses regarding this failure have been developed showing an agonist activity in place of an antagonist activity of these molecules (Veldscholte J, Berrevoets C A, Brinkmann A O, Grootegoed J A, Mulder E. Biochemistry 1992 Mar. 3; 31(8): 2393-9). For example, nilutamide is capable of stimulating the growth of human prostate cancer cells in culture. In addition to these experimental indications, clinical data also support this deleterious role of the anti-androgens (Akimoto S.; Antiandrogen withdrawal syndrome Nippon Rinsho. 1998 August; 56(8):2135-9. Paul R, Breul J. Antiandrogen withdrawal syndrome associated with prostate cancer therapies: incidence and clinical significance Drug Saf. 2000 November; 23(5):381-90).

In this case the Applicant has identified compounds showing an anti-proliferative activity for the prostatic tumour which surprisingly does not show agonist activity at concentrations where the nilutamide behaves as an agonist. This difference in the novel compounds' behaviour with respect to proliferation compared with that of nilutamide is supported by their ability to induce the disappearance of androgen receptors in their protein form. Nilutamide has no effect on this receptor level.

The properties of these novel molecules must allow better management of prostate cancer avoiding the failure of current anti-androgens.

Moreover, the compounds of the present invention can also be used for treating pathologies linked to the presence of androgen receptors such as for example benign prostatic hyperplasia, prostamegaly, acne, androgenic alopecia, hirsutism etc.

SUMMARY OF THE INVENTION

A subject of the invention is therefore the compounds of general formula (I)

in which:
$R^1$ represents a cyano, nitro, amino, —NHCOOR$^4$ or —NHCOR$^4$ radical;
$R^2$ represents a halo, alkyl, haloalkyl, or alkoxy radical;
$R^3$ represents an alkyl radical or a hydrogen atom; or the two $R^3$ radicals form together with the carbon atom to which they are attached a cycloalkyl comprising 3 to 4 members;
X represents
  either a linear or branched alkylene chain with 3 to 7 carbon atoms, this chain being able to contain one or more additional identical or different members chosen from —O—, —N(R$^5$)—, —S—, —SO— or —SO$_2$—; or
  or a group,
where n1 and p1 are two integers the sum of which n1+p1 is an integer chosen from 2, 3, 4 or 5;
$R^6$ and $R^7$ form together a covalent bond, or $R^6$ and $R^7$ form together with the carbon atoms to which they are connected the ring or a cycloalkyl comprising 3 to 6 members;
$R^4$ represents an alkyl, aryl, or heteroaryl radical;
$R^5$ represents a hydrogen, an alkyl, or aralkyl radical;
or a pharmaceutically acceptable salt thereof.

Preferably, X represents a linear or branched alkylene chain with 3 to 7 carbon atoms, this chain being able to contain one or more additional identical or different members chosen from —O—, —N(R$^5$)—, —S—, —SO— or —SO$_2$—.

More preferentially, X represents an alkylene chain being able to contain a single member chosen from —O—, —N(R$^5$)—, —S—, —SO— or —SO$_2$—.

According to a variant, X represents a group,
where n1 and p1 are two integers the sum of which n1+p1 is an integer chosen from 2, 3, 4 and 5;
R$^6$ and R$^7$ form together a covalent bond, or R$^6$ and R$^7$ form together with the carbon atoms to which they are connected the ring or a cycloalkyl comprising 3 to 6 members;
Preferably, n1 and p1 are equal.
Preferably, the sum n1+p1 is equal to 2. Preferably, the sum n1+p1 is equal to 3. Preferably, the sum n1+p1 is equal to 4. Preferably, the sum n1+p1 is equal to 5.

According to another variant, X represents a group, and X' represents an —O—, —N(R$^5$)— or —S—, —SO—, —SO$_2$—, —CH$_2$— or group, and n2 and p2 are integers the sum of which n2+p2 is either an integer chosen from 3, 4, 5, 6 and 7 when X' represents an —O—, —N(R$^5$)—, —S—, —SO—, —SO$_2$— group or an integer chosen from 2, 3, 4 and 5 when X' represents a —CH$_2$— or group.
Preferably, X' represents a group.
Preferably, X' represents an —O—, —N(R$^5$)— or —(CH$_2$)— group.
Preferably, n2 and p2 are equal.

Preferably, the sum n2+p2 is equal to 2. Preferably, the sum n2+p2 is equal to 3. Preferably, the sum n2+p2 is equal to 4. Preferably, the sum n2+p2 is equal to 5. Preferably, the sum n2+p2 is equal to 6. Preferably, the sum n2+p2 is equal to 7.

Preferably, R$^3$ represents an alkyl radical or the two R$^3$ radicals form together with the carbon atom to which they are attached a cycloalkyl comprising 3 to 4 members.

Preferably, R$^4$ represents an alkyl radical.
Preferably, R$^5$ represents an alkyl radical.
Preferably, X represents a linear alkylene chain with 3 to 7 carbon atoms.
Preferably, R$^1$ is in para position.
Preferably, R$^2$ is in meta position.
Preferably, R$^2$ represents a haloalkyl radical.
Preferably, R$^6$ and R$^7$ form together a covalent bond.
Preferably, R$^6$ and R$^7$ form together with the carbon atoms to which they are connected the ring.
Preferably, R$^6$ and R$^7$ form together with the carbon atoms to which they are connected a cycloalkyl comprising 3 to 6 members.

According to another variant, R$^3$ represents an alkyl radical or a hydrogen; and preferentially an alkyl radical.
Preferentially, R$^4$ represents an alkyl radical and R$^5$ represents an alkyl radical.
Preferentially,
R$^1$ represents a cyano, nitro, amino, —NHCOOR$^4$ or —NHCOR$^4$ radical;
R$^2$ represents a halo, alkyl, haloalkyl, alkoxy radical;
R$^3$ represents an alkyl radical;
X represents a linear or branched alkylene chain with 3 to 7 carbon atoms, this chain being able to contain an additional —O— or —N(R$^5$)— member;
R$^4$ represents an alkyl radical;
and R$^5$ represents an alkyl radical.
Even more preferentially, R$^1$ represents a cyano, nitro, or —NHCOOR$^4$ radical.
Very preferentially also, X represents an alkylene chain with 4 to 7 carbon atoms, this chain being able to contain an additional —O— member.
Preferably, the alkyl radical represents a methyl group.
The compound of formula (I) is preferably chosen from:
1,1'-butane-1,4-diylbis{5,5-dimethyl-3-[4-nitro-3-(trifluoromethyl)phenyl]imidazolidine-2,4-dione}
1,1'-pentane-1,5-diylbis{5,5-dimethyl-3-[4-nitro-3-(trifluoromethyl)phenyl]imidazolidine-2,4-dione}
1,1'-hexane-1,6-diylbis{5,5-dimethyl-3-[4-nitro-3-(trifluoromethyl)phenyl]imidazolidine-2,4-dione}
1,1'-heptane-1,7-diylbis{5,5-dimethyl-3-[4-nitro-3-(trifluoromethyl)phenyl]imidazolidine-2,4-dione}
4,4'-[pentane-1,5-diylbis(4,4-dimethyl-2,5-dioxoimidazolidine-3,1-diyl)]bis[2-(trifluoromethyl)benzonitrile]
1,1'-(3-methylpentane-1,5-diyl)bis{5,5-dimethyl-3-[4-nitro-3-(trifluoromethyl)phenyl]imidazolidine-2,4-dione}
1,1'-(oxydiethane-2,1-diyl)bis{5,5-dimethyl-3-[4-nitro-3-(trifluoromethyl)phenyl]imidazolidine-2,4-dione}
1,1'-pentane-1,5-diylbis{3-[4-amino-3-(trifluoromethyl)phenyl]-5,5-dimethylimidazolidine-2,4-dione}
N,N'-(pentane-1,5-diylbis{(4,4-dimethyl-2,5-dioxoimidazolidine-3,1-diyl)[2-(trifluoromethyl)-4,1-phenylene]})diacetamide 1,1'-pentane-1,5-diylbis[5,5-dimethyl-3-(3-methyl-4-nitrophenyl)imidazolidine-2,4-dione]
1,1'-pentane-1,5-diylbis{5,5-dimethyl-3-[4-nitro-2-(trifluoromethyl)phenyl]imidazolidine-2,4-dione}
1,1'-pentane-1,5-diylbis[3-(3-chloro-4-nitrophenyl)-5,5-dimethyl-imidazolidine-2,4-dione]
1,1'-pentane-1,5-diylbis[3-(3-methoxy-4-nitrophenyl)-5,5-dimethyl-imidazolidine-2,4-dione]
dimethyl {pentane-1,5-diylbis[(4,4-dimethyl-2,5-dioxoimidazolidine-3,1-diyl)(2-methyl-4,1-phenylene)]}biscarbamate
4,4'-[pentane-1,5-diylbis(4,4-dimethyl-2,5-dioxoimidazolidine-3,1-diyl)]bis(2-methylbenzonitrile)
4,4'-[pentane-1,5-diylbis(4,4-dimethyl-2,5-dioxoimidazolidine-3,1-diyl)]bis(2-chlorobenzonitrile)
1,1'-propane-1,3-diylbis{5,5-dimethyl-3-[4-nitro-3-(trifluoromethyl)phenyl]imidazolidine-2,4-dione}
2-{5,5-dimethyl-3-[4-nitro-3-(trifluoromethyl)phenyl]-2,4-dioxoimidazolidin-1-yl}-N-(2-{5,5-dimethyl-3-[4-nitro-3-(trifluoromethyl)-phenyl]-2,4-dioxoimidazolidin-1-yl}ethyl)-N-methylethanamine
1,1'-(2Z)-but-2-ene-1,4-diylbis{5,5-dimethyl-3-[4-nitro-3-(trifluoromethyl)phenyl]imidazolidine-2,4-dione}
4,4'-[pentane-1,5-diylbis(5,7-dioxo-4,6-diazaspiro[2.4]heptane-4,6-diyl)]bis[2-(trifluoromethyl)benzonitrile]
4,4'-[(2Z)-but-2-ene-1,4-diylbis(4,4-dimethyl-2,5-dioxoimidazolidine-3,1-diyl)]bis[2-(trifluoromethyl)benzonitrile]
4,4'-{(2R,3S)-oxirane-2,3-diylbis[methanediyl(4,4-dimethyl-2,5-dioxoimidazolidine-3,1-diyl)]}bis[2-(trifluoromethyl)benzonitrile]
4,4'-{(1R,2R)-cyclopropane-1,2-diylbis[methanediyl(4,4-dimethyl-2,5-dioxoimidazolidine-3,1-diyl)]}bis[2-(trifluoromethyl)benzonitrile]
or a pharmaceutically acceptable salt of this compound;
In particular, the compound of formula (I) is chosen from:
1,1'-butane-1,4-diylbis{5,5-dimethyl-3-[4-nitro-3-(trifluoromethyl)phenyl]imidazolidine-2,4-dione}
1,1'-pentane-1,5-diylbis{5,5-dimethyl-3-[4-nitro-3-(trifluoromethyl)phenyl]imidazolidine-2,4-dione}
1,1'-hexane-1,6-diylbis{5,5-dimethyl-3-[4-nitro-3-(trifluoromethyl)phenyl]imidazolidine-2,4-dione}
1,1'-heptane-1,7-diylbis{5,5-dimethyl-3-[4-nitro-3-(trifluoromethyl)phenyl]imidazolidine-2,4-dione}
4,4'-[pentane-1,5-diylbis(4,4-dimethyl-2,5-dioxoimidazolidine-3,1-diyl)]bis[2-(trifluoromethyl)benzonitrile]
1,1'-(3-methylpentane-1,5-diyl)bis{5,5-dimethyl-3-[4-nitro-3-(trifluoromethyl)phenyl]imidazolidine-2,4-dione}
1,1'-(oxydiethane-2,1-diyl)bis{5,5-dimethyl-3-[4-nitro-3-(trifluoromethyl)phenyl]imidazolidine-2,4-dione}
1,1'-pentane-1,5-diylbis{3-[4-amino-3-(trifluoromethyl)phenyl]-5,5-dimethylimidazolidine-2,4-dione}
N,N'-(pentane-1,5-diylbis{(4,4-dimethyl-2,5-dioxoimidazolidine-3,1-diyl)[2-(trifluoromethyl)-4,1-phenylene]})diacetamide
1,1'-pentane-1,5-diylbis[5,5-dimethyl-3-(3-methyl-4-nitrophenyl)imidazolidine-2,4-dione]
1,1'-pentane-1,5-diylbis{5,5-dimethyl-3-[4-nitro-2-(trifluoromethyl)phenyl]imidazolidine-2,4-dione}
1,1'-pentane-1,5-diylbis[3-(3-chloro-4-nitrophenyl)-5,5-dimethyl-imidazolidine-2,4-dione]
1,1'-pentane-1,5-diylbis[3-(3-methoxy-4-nitrophenyl)-5,5-dimethyl-imidazolidine-2,4-dione]
dimethyl {pentane-1,5-diylbis[(4,4-dimethyl-2,5-dioxoimidazolidine-3,1-diyl)(2-methyl-4,1-phenylene)]}biscarbamate
4,4'-[pentane-1,5-diylbis(4,4-dimethyl-2,5-dioxoimidazolidine-3,1-diyl)]bis(2-methylbenzonitrile)
4,4'-[pentane-1,5-diylbis(4,4-dimethyl-2,5-dioxoimidazolidine-3,1-diyl)]bis(2-chlorobenzonitrile)
1,1'-propane-1,3-diylbis{5,5-dimethyl-3-[4-nitro-3-(trifluoromethyl)phenyl]imidazolidine-2,4-dione}
2-{5,5-dimethyl-3-[4-nitro-3-(trifluoromethyl)phenyl]-2,4-dioxoimidazolidin-1-yl}-N-(2-{5,5-dimethyl-3-[4-nitro-3-(trifluoromethyl)-phenyl]-2,4-dioxoimidazolidin-1-yl}ethyl)-N-methylethanamine
1,1'-(2Z)-but-2-ene-1,4-diylbis{5,5-dimethyl-3-[4-nitro-3-(trifluoromethyl)phenyl]imidazolidine-2,4-dione}
4,4'-[pentane-1,5-diylbis(5,7-dioxo-4,6-diazaspiro[2.4]heptane-4,6-diyl)]bis[2-(trifluoromethyl)benzonitrile]
4,4'[(2Z)-but-2-ene-1,4-diylbis(4,4-dimethyl-2,5-dioxoimidazolidine-3,1-diyl)]bis[2-(trifluoromethyl)benzonitrile]
4,4'-{(2R,3S)-oxirane-2,3-diylbis[methanediyl(4,4-dimethyl-2,5-dioxoimidazolidine-3,1-diyl)]}bis[2-(trifluoromethyl)benzonitrile]
4,4'-{(1R,2R)-cyclopropane-1,2-diylbis[methanediyl(4,4-dimethyl-2,5-dioxoimidazolidine-3,1-diyl)]}bis[2-(trifluoromethyl)benzonitrile]
or a pharmaceutically acceptable salt of this compound;
Preferably, the compound of general formula (I) is chosen from:
1,1'-butane-1,4-diylbis{5,5-dimethyl-3-[4-nitro-3-(trifluoromethyl)phenyl]imidazolidine-2,4-dione}
1,1'-pentane-1,5-diylbis{5,5-dimethyl-3-[4-nitro-3-(trifluoromethyl)phenyl]imidazolidine-2,4-dione}
1,1'-(oxydiethane-2,1-diyl)bis{5,5-dimethyl-3-[4-nitro-3-(trifluoromethyl)phenyl]imidazolidine-2,4-dione}
4,4'-[pentane-1,5-diylbis(4,4-dimethyl-2,5-dioxoimidazolidine-3,1-diyl)]bis(2-methylbenzonitrile)
1,1'-(2Z)-but-2-ene-1,4-diylbis{5,5-dimethyl-3-[4-nitro-3-(trifluoromethyl)phenyl]imidazolidine-2,4-dione}
or a pharmaceutically acceptable salt thereof.
More particularly the compound of formula (I) is chosen from:
1,1'-butane-1,4-diylbis{5,5-dimethyl-3-[4-nitro-3-(trifluoromethyl)phenyl]imidazolidine-2,4-dione}
1,1'-pentane-1,5-diylbis{5,5-dimethyl-3-[4-nitro-3-(trifluoromethyl)phenyl]imidazolidine-2,4-dione}
1,1'-(oxydiethane-2,1-diyl)bis{5,5-dimethyl-3-[4-nitro-3-(trifluoromethyl)phenyl]imidazolidine-2,4-dione}
4,4'-[pentane-1,5-diylbis(4,4-dimethyl-2,5-dioxoimidazolidine-3,1-diyl)]bis(2-methylbenzonitrile).
1,1'-(2Z)-but-2-ene-1,4-diylbis{5,5-dimethyl-3-[4-nitro-3-(trifluoromethyl)phenyl]imidazolidine-2,4-dione}
or a pharmaceutically acceptable salt of this compound.

Preferably, the compound of general formula (I) is 1,1'-pentane-1,5-diylbis{5,5-dimethyl-3-[4-nitro-3-(trifluoromethyl)-phenyl]imidazolidine-2,4-dione} or 1,1'-(2Z)-but-2-ene-1,4-diylbis{5,5-dimethyl-3-[4-nitro-3-(trifluoromethyl)phenyl]imidazolidine-2,4-dione}.

Quite particularly, the compound of formula (I) is 1,1'-pentane-1,5-diylbis{5,5-dimethyl-3-[4-nitro-3-(trifluoromethyl)-phenyl]imidazolidine-2,4-dione}.

A subject of the invention is also a process for the preparation of a compound of formula (I), comprising a stage which consists of
(i) condensing two equivalents of the arylhydantoins of general formula (II)

(II)

in which $R^2$ and $R^3$ are as defined previously and $R^1$ is a nitro or cyano group, with a derivative of general formula $Gp^1$—X—$Gp^2$, $Gp^1$ and $Gp^2$ being leaving groups, and X being as defined previously, in the presence of a strong base, in order to form the compound of general formula (I)

(I)

in which $R^2$, $R^3$ and X are as defined previously and $R^1$ is a nitro or cyano group.

Preferably, the condensation is carried out by heating the reaction mixture to a temperature comprised between 20 and 100° C., preferably, between 45 and 65° C.

Preferably, the reaction is carried out in an aprotic polar solvent.

Preferably, the process comprises moreover a stage of (ii) reducing the nitro group in order to obtain a compound of formula (III)

(III)

Preferably, the process comprises moreover a stage which consists of (iii) reacting a compound of formula (III) obtained in stage (ii) with an acid chloride of general formula $R^4$—COCl in which $R^4$ is as defined previously in order to obtain a compound of formula (IV)

(IV)

According to a variant, the process comprises moreover a stage which consists of (iv) reacting a compound obtained in stage (ii) with a chloroformate of general formula $R^4$—O—CO—Cl in which $R^4$ is as defined previously in order to obtain a compound of formula (V)

(V)

According to another variant, if $R^6$ and $R^7$ form together a covalent bond, the process can moreover comprise a stage of:

(v) oxidizing the compound of formula (I) in which $R^6$ and $R^7$ form together a covalent bond, the double bond thus formed by $R^6$ and $R^7$ in order to obtain a compound of formula (VI)

(VI)

The invention also relates to a compound of formula (I) as medicament.

The invention also relates to the pharmaceutical compositions containing, as active ingredient, at least one compound of formula (I) in combination with a pharmaceutically acceptable support.

The invention also relates to the use of a compound of formula (I), for the preparation of a medicament intended to treat cancers.

Preferably, the medicament is intended to treat a hormone-dependent cancer.

Preferably, the medicament is intended to treat a cancer expressing androgen receptors Preferably, the medicament is intended to treat a cancer of the breast or the prostate, preferably, cancer of the prostate.

DETAILED DESCRIPTION OF EMBODIMENTS OF THE INVENTION

Therefore a subject of the invention is the compounds of general formula (I)

(I)

in which $R^1$ represents a cyano, nitro, amino, —NHCOOR$^4$ or —NHCOR$^4$ radical.

$R^2$ represents a halo, alkyl, haloalkyl, alkoxy radical. $R^3$ represents an alkyl radical or a hydrogen. Alternatively, the two $R^3$ radicals form together with the carbon atom to which they are attached a cycloalkyl radical comprising 3 to 4 members.

X represents a linear or branched alkylene chain with 3 to 7 carbon atoms, this chain being able to contain one or more additional identical or different members —O—, —N(R$^5$)— or —S—, —SO— or —SO$_2$—. Alternatively, X represents a group, where n1 and p1 are two integers the sum of which n1+p1 is comprised between 2 and 5. For example, n1 and p1 are each equal to 1 or 2, preferably n1 and p1 equal 1.

$R^6$ and $R^7$ form together a covalent bond. In this case, X then represents a (CH$_2$)n1-CH═CH—(CH$_2$)p1 group.

Alternatively, $R^6$ and $R^7$ form together with the carbon atoms to which they are connected a ring. According to another alternative, $R^6$ and $R^7$ form together with the carbon atoms to which they are connected a cycloalkyl radical comprising 3 to 6 members, for example, a cyclobutyl, a cyclopentyl or a cyclohexyl.

$R^4$ represents an alkyl, aryl, or heteroaryl radical.

$R^5$ represents a hydrogen, an alkyl or aralkyl radical.

The compounds of formula (I) can be in the form of a pharmaceutically acceptable salt.

By pharmaceutically acceptable salt, is meant in particular addition salts of inorganic acids such as hydrochloride, hydrobromide, sulphate, phosphate, diphosphate and nitrate or organic acids such as acetate, maleate, fumarate, tartrate, succinate, citrate, lactate, methanesulphonate, benzenesulphonate, p-toluenesulphonate, pamoate and stearate. Also included within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

In the definitions indicated above, the expression halogen (or halo) represents the fluoro, chloro, bromo or iodo radical, preferably chloro, fluoro or bromo.

Unless otherwise specified, the term alkyl within the meaning of the present invention represents a linear or branched alkyl radical comprising between 1 and 12 carbon atoms such as the methyl, ethyl, propyl, isopropyl, butyl, isobutyl, sec-butyl and tert-butyl, pentyl or amyl, isopentyl, neopentyl, hexyl or isohexyl, heptyl, octyl, nonyl, decyl, undecyl or dodecyl radicals. Preferentially the alkyl radical is a (C$_1$-C$_6$) alkyl radical, i.e. representing an alkyl radical having 1 to 6 carbon atoms as defined above, or a (C$_1$-C$_4$)alkyl radical representing an alkyl radical having 1 to 4 carbon atoms such as for example the methyl, ethyl, propyl, isopropyl, butyl, isobutyl, sec-butyl and tert-butyl radicals. Very preferentially, the alkyl radical is the methyl radical.

The term alkyl in the expressions alkoxy (or alkyloxy), or haloalkyl represents an alkyl radical as defined above.

More particularly, by haloalkyl, is meant an alkyl radical at least one (and optionally all) of the hydrogen atoms of which is replaced by a halogen atom (halo) such as for example, and preferentially trifluoromethyl.

By cycloalkyl unless otherwise specified, is meant a saturated cyclic carbon radical comprising 3 to 6 members such as the cyclopropyl or cyclobutyl.

Within the meaning of the present invention, the aryl radicals can be of mono or polycyclic aromatic type. The monocyclic aryl radicals can be chosen from the phenyl, tolyl, xylyl, mesityl, cumenyl and preferably phenyl radicals. The polycyclic aryl radicals can be chosen from the naphthyl, anthryl, phenanthryl, fluorenyl radicals. They can be optionally substituted by one or more identical or different radicals such as alkyl, haloalkyl, alkoxy, alkoxycarbonyl, alkylcarbonyloxy, halo, cyano, nitro, aryl, aryloxy, aryloxycarbonyl, or arylcarbonyloxy.

Within the meaning of the present invention, the term aralkyl represents an alkyl radical as defined previously substituted by an aryl radical as defined above.

Within the meaning of the present invention, the term heteroaryl designates an unsaturated aromatic ring comprising one or more identical or different heteroatoms chosen from N, O and S such as furyl, thienyl isoxazolyl, benzothiadiazolyl, pyridinyl, oxazolyl, pyrazolyl, pyrimidinyl or quinoxalyl.

A subject of the invention is also a process for the preparation of a compound of formula (I), comprising a stage which consists of

(i) condensing two equivalents of the arylhydantoins of general formula (II)

(II)

in which $R^2$ and $R^3$ are as defined previously and $R^1$ is a nitro or cyano group, with a derivative of general formula Gp$^1$—X—Gp$^2$, Gp$^1$ and Gp$^2$ being leaving groups, and X being as defined previously, in the presence of a strong base, in order to form the compound of general formula (I)

(I)

in which $R^2$, $R^3$ and X are as defined previously and $R^1$ is a nitro or cyano group.

A) Preparation of the Compounds in which $R^1$ is a Nitro Group or Cyano:

The compounds of general formula (I) according to the invention can be prepared according to the synthesis route represented in Diagram 1, below. The compounds of general formula (I) in which $R^1$, $R^2$, $R^3$ and X are as described above can be obtained in one stage by the condensation of two equivalents of the arylhydantoin intermediates of general formula (II) with a derivative of general formula $Gp^1$—X—$Gp^2$, $Gp^1$ and $Gp^2$ being considered as leaving groups, and X being as defined previously, such as for example a halogen group or a sulphonate group. This condensation is carried out in the presence of a base, such as for example NaH. Preferably, the condensation is carried out by heating the reaction mixture to a temperature comprised between 20 and 100° C., preferably between 45 and 65° C. Preferably, the condensation is carried out in a polar solvent, preferably in an aprotic polar solvent such as for example THF, DMF or DMSO. Generally, the reaction is carried out for a duration varying from 1 to 15 hours.

Diagram 1

-continued (I)

A.1) Preparation of the Compounds in which $R^1$ is an Amino Group

In the particular case where $R^1$ is a nitro group, $R^2$, $R^3$ and X being as described above, the preparation of the aniline derivatives of general formula $(I)_{A1}$ is represented in Diagram A1. The reduction of the nitro groups is carried out using $SnCl_2$, $2H_2O$ (*J. Heterocyclic Chem.* 1987, 24, 927-930; *Tetrahedron Letters* 1984, 25 (8), 839-842) in an appropriate solvent such as ethyl acetate.

Diagram A1

A.2) Preparation of the Compounds in which $R^1$ is an Acetamide Group:

The acetamide derivatives of general formula $(I)_{A2}$ in which $R^2$, $R^3$, $R^4$ and X are as described above, are accessible in one stage from the aniline derivatives of general formula $(I)_{A1}$, Diagram A2. The acylation reaction can be carried out using a large excess of acid chloride of general formula $R^4$—COCl, for example acetyl chloride, or an anhydride of $(R^4$—CO$)_2$O type, such as acetic anhydride, and using this reagent in excess as solvent.

Diagram A2

A.3) Preparation of the Compounds in which $R^1$ is a Carbamate Group:

The carbamate derivatives of general formula $(I)_{A3}$ in which $R^2$, $R^3$, $R^4$ and X are as described above, are prepared in one stage from the aniline derivatives of general formula $(I)_{A1}$, Diagram A3. The formation of the carbamate is carried out using a large excess of a chloroformate of general formula $R^4$—O—CO—Cl, in the presence of an anhydrous solvent, preferably an anhydrous aprotic polar solvent. Preferably, anhydrous pyridine is used. The reaction generally takes place by heating to a temperature comprised between 60 and 100° C. and for a duration of 12 to 24 hours.

B) Preparation of the Intermediates of General Formula (II):

The synthesis of the arylhydantoin intermediates of general formula (II) in which $R^1$, $R^2$ and $R^3$ are as described above can be carried out according to the strategies described in the diagrams below:

B.1) Preparation of the Arylhydantoins by Condensation:

The synthesis of the arylhydantoin of general formula (II), Diagram B1, can be carried out by nucleophilic substitution of the fluorine atom borne by the aromatic ring of the compound of general formula $(II)_1$ by the anion of the hydantoin of general formula $(II)_2$ generated in the presence of a base such as, for example $K_2CO_3$. The reaction is carried out by heating at a temperature comprised between 65 and 140° C. and in a polar aprotic solvent such as, for example, DMF or DMSO. The temperature and the reaction time are a function of the nucleofugal character of the fluorine atom which is highly dependent on the nature of $R^1$ and $R^2$. The hydantoins of general formula $(II)_2$ that are not commercially available can be prepared according to the methods described in the literature (e.g. *J. Med. Chem.* 1984, 27 (12), 1663-8).

Diagram A3

A.4) Preparation of the Compounds in which X Contains an Oxirane.

In the particular case where X contains a double bond, $R^1$, $R^2$ and $R^3$ being as described above, the compounds of general formulae $(I)_{A4}$ can be obtained by oxidizing the compounds of general formula (I) with an appropriate oxidizing agent such as for example perbenzoic acid or peracetic acid in an aprotic solvent, The reaction generally takes place at ambient temperature and for a duration of 1 to 4 days.

Diagram A4

Diagram B1

In the cases where $R^1$ et $R^2$ are not sufficiently electro-attractive to promote the aromatic nucleophilic substitution described in Diagram B1, an approach by coupling between an aryl boronic acid and the hydantoin of general formula $(II)_2$ in the presence of copper acetate can be envisaged (*Synlett* 2006, 14, 2290-2) in order to obtain the compounds of general formula (II).

B.2) Preparation of the Arylhydantoins by Construction of the Hydantoin Ring from Arylisocyanate:

Access to the hydantoins of general formula (II) is carried out, in this case, according to a protocol described in *Bioorg. Med. Chem. Lett.* 2004, 14, 5285.

B.3) Preparation of the Arylhydantoins by Cyclization from the Arylureas

The synthesis of the arylhydantoin intermediates of general formula (II), Diagram B3, in which $R^1$, $R^2$ and $R^3$ are as described above can be carried out by cyclization of an intermediate of general formula $(II)_3$ prepared according to methods described in the literature (for example Organic Process Research & Development 2002, 6, 759-761). The cyclization reaction can be carried out by the intermediate formation of the acyl halide then by heating. The acyl halide being able to be generated by a halogenation agent such as for example oxalyl chloride or thionyl chloride in an aprotic solvent such as for example 1-4, dioxane or tetrahydrofuran.

Diagram B3

B.4) Preparation of the Arylhydantoins by Construction of the Hydantoin Ring from the Aminoester Isocyanates:

Alternatively, the arylhydantoins of general formula (II) can be synthesized from aminoester isocyanates as described in *Eur. J. Med. Chem.* 1984, 19 (3), 261.

The salification of the compounds of formula (I) can be carried out by any method known to a person skilled in the art. For example, the salification can be carried out by the addition of a base or acid, for example, sodium or potassium hydroxide, or hydrochloric acid.

The compounds of formula (I) according to the present invention have useful pharmacological properties. In fact, it has been discovered that the compounds of formula (I) of the present invention have an anti-tumour (anti-cancer) activity, and more particularly an inhibitory activity on the cell proliferation of the cells expressing androgen receptors such as the LnCAP type prostatic cells. Thus, the compounds of the present invention can be used in different therapeutic applications. They can advantageously be used for the treatment of cancers, particularly hormone-dependent cancers, cancers expressing androgen receptors and more particularly breast and prostate cancers. An illustration of the pharmacological properties of the compounds of the invention will be found hereafter in the experimental part.

Therefore, a subject of the present application is also the compounds of formula (I) as defined previously as medicaments.

Also, a subject of the present application is the compounds of formula (I) as defined previously as medicaments intended to treat the proliferative diseases, preferentially cancers, very preferentially hormone-dependent cancers or cancers expressing androgen receptors, or also prostate and breast cancers and very preferentially prostate cancers.

A subject of the present application is also pharmaceutical compositions containing, as active ingredient, at least one compound of formula (I) as defined above, in combination with a pharmaceutically acceptable support.

A subject of the present application is also the use of a compound of formula (I) according to the present invention, for the preparation of an anti-tumour medicament.

A subject of the present application is also the use of a compound of formula (I) according to the present invention, for the preparation of a medicament intended to inhibit cell proliferation.

A subject of the present application is also the use of a compound of formula (I) according to the present invention, for the preparation of a medicament intended to treat proliferative diseases, preferentially cancers, very preferentially hormone-dependent cancers or cancers expressing androgen receptors, or prostate and breast cancers and very preferentially prostate cancers.

The pharmaceutical composition can be in the form of a solid, for example powders, granules, tablets, gelatin capsules. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or glycols, as well as their mixtures, in varying proportions, in water added to pharmaceutically acceptable oils or fats. The sterile liquid compositions can be used for intramuscular, intraperitoneal or sub-cutaneous injections and the sterile compositions can also be administered by intravenous route.

All the technical and scientific terms used in the present text have the meaning known to a person skilled in the art. Moreover, all the patents (or patent applications) as well as the other bibliographical references are incorporated by way of reference Experimental Part Following the definitions of the variables $R^1$, $R^2$, $R^3$ and X, the compounds according to the invention can be prepared according to the different methods described above.

The NMR analyses of Examples 1 to 23 were carried out on a 400 MHz Bruker-Avance II spectrometer.

The examples are presented in order to illustrate the above procedures and should in no event be considered as a limit to the scope of the invention.

The terminology used for the nomenclature of the compounds below and the examples is the IUPAC terminology.

Example 1

1,1'-butane-1,4-diylbis{5,5-dimethyl-3-[4-nitro-3-(trifluoromethyl)phenyl]imidazolidine-2,4-dione}

NaH (at 60%) (22 mg, 0.55 mmole) is added under argon to a solution of 5,5-dimethyl-3-[4-nitro-3-(trifluoromethyl)phenyl]-imidazolidine-2,4-dione (158 mg, 0.5 mmole) in anhydrous DMF (8 ml). A gas release accompanies the change of colour of the reaction medium which becomes orange. Stirring is maintained for 30 minutes at 23° C. before the addition of 1,4-dibromobutane (30 μl, 0.25 mmole). The reaction mixture is heated at 55° C. for 1 hour before being poured into a saturated aqueous solution of $NH_4Cl$ (25 ml) and extracted with AcOEt (2×25 ml). The organic phases are combined and washed successively with water (25 ml) and salt water (25 ml). After drying over $Na_2SO_4$, the organic solution is filtered and concentrated under vacuum. The evaporation residue is purified on a silica column (eluent: Heptane/AcOEt: 4/6 to 1/9).

The expected compound is obtained in the form of a light yellow coloured solid with a yield of 45%. Melting point: 211-212° C.

$^1$H NMR 400 MHz (DMSO-$d_6$) δ: 8.32 (d, 2H, Ph); 8.21 (d, 2H, Ph); 8.08 (dd, 2H, Ph); 3.39 (m, 4H, 2×$NCH_2$); 1.70 (m, 4H, 2×$CH_2$); 1.49 (s, 12H, 4×$CH_3$).

Example 2

1,1'-pentane-1,5-diylbis{5,5-dimethyl-3-[4-nitro-3-(trifluoromethyl)phenyl]imidazolidine-2,4-dione}

The experimental protocol used is the same as that described for the synthesis of the compound of Example 1, 1,5-diiodopentane replacing 1,4-dibromobutane. The expected compound is obtained in the form of a white solid with a yield of 40%. Melting point: 163-164° C.

$^1$H NMR 400 MHz (DMSO-$d_6$) δ: 8.33 (d, 2H, Ph); 8.21 (d, 2H, Ph); 8.07 (d, 2H, Ph); 3.34 (m, 4H, 2×$NCH_2$); 1.69 (m, 4H, 2×$CH_2$); 1.50 (s, 12H, 4×$CH_3$); 1.41 (m, 2H, $CH_2$).

Example 3

1,1'-hexane-1,6-diylbis{5,5-dimethyl-3-[4-nitro-3-(trifluoromethyl)phenyl]imidazolidine-2,4-dione}

The experimental protocol used is the same as that described for the synthesis of the compound of Example 1, 1,6-diiodohexane replacing 1,4-dibromobutane. The expected compound is obtained in the form of a light yellow solid with a yield of 27%. Melting point: 187-188° C.

$^1$H NMR 400 MHz (DMSO-$d_6$) δ: 8.31 (broad d, 2H, Ph); 8.20 (broad s, 2H, Ph); 8.07 (broad d, 2H, Ph); 3.32 (m, 4H, 2×$NCH_2$); 1.64 (m, 4H, 2×$CH_2$); 1.46 (s, 12H, 4×$CH_3$); 1.38 (m, 4H, 2×$CH_2$).

Example 4

1,1'-heptane-1,7-diylbis{5,5-dimethyl-3-[4-nitro-3-(trifluoromethyl)phenyl]imidazolidine-2,4-dione}

The experimental protocol used is the same as that described for the synthesis of the compound of Example 1, 1,7-dibromoheptane replacing 1,4-dibromobutane. The expected compound is obtained in the form of a light yellow solid with a yield of 35%. Melting point: 137-138° C.

$^1$H NMR 400 MHz (DMSO-$d_6$) δ: 8.31 (d, 2H, Ph); 8.19 (d, 2H, Ph); 8.06 (dd, 2H, Ph); 3.30 (m, 4H, 2×$NCH_2$); 1.64 (m, 4H, 2×$CH_2$); 1.46 (s, 12H, 4×$CH_3$); 1.36 (m, 6H, 3×$CH_2$).

Example 5

4,4'-[pentane-1,5-diylbis(4,4-dimethyl-2,5-dioxoimidazolidine-3,1-diyl)]bis[2-(trifluoromethyl)benzonitrile]

5.1) 4-(4,4-dimethyl-2,5-dioxoimidazolidin-1-yl)-2-(trifluoromethyl)benzonitrile A mixture of 4-fluoro-2-(trifluoromethyl)benzonitrile (5.67 g, 30 mmoles), 5,5-dimethyl-hydantoin (7.68 g, 60 mmoles), $K_2CO_3$ (8.28 g, 60 mmoles) in DMF (45 ml) is distributed in equal parts into three tubes to be placed in a microwave oven. Under magnetic stirring, each tube is irradiated at 140° C. for 20 minutes. The reaction masses are then combined, poured into water (200 ml) and extracted with AcOEt (2×75 ml). The organic phases are combined, washed with salt water, dried over $Na_2SO_4$ and filtered. The filtrate is concentrated under reduced pressure and the residue crystallizeds from Et2O (25 ml). After recrystallization from EtOH (75 ml), the powder is filtered and dried under vacuum. The expected compound is obtained in the form of a white solid with a yield of 46% (4.1 g). Melting point: 212-213° C.

$^1$H NMR 400 MHz (DMSO-$d_6$) δ: 8.80 (s, 1H, NH); 8.29 (d, 1H, Ph); 8.18 (s, 1H, Ph); 8.02 (d, 1H, Ph); 1.42 (s, 6H, 2×$CH_3$).

5.2) 4,4'-[pentane-1,5-diylbis(4,4-dimethyl-2,5-dioxoimidazolidine-3,1-diyl)]bis[2-(trifluoromethyl)benzonitrile]

The experimental protocol used is the same as that described for the synthesis of the compound of Example 2, intermediate 5.1 replacing 5,5-dimethyl-3-[4-nitro-3-(trifluoromethyl)-phenyl]-imidazolidine-2,4-dione. The expected compound is obtained in the form of a white solid with a yield of 50% (330 mg). Melting point: 167-169° C.

$^1$H NMR 400 MHz (DMSO-$d_6$) δ: 8.28 (d, 2H, Ph); 8.18 (s, 2H, Ph); 8.02 (d, 2H, Ph); 3.30 (m, 4H, 2×$NCH_2$); 1.67 (m, 4H, 2×$CH_2$); 1.46 (s, 12H, 4×$CH_3$); 1.40 (m, 2H, $CH_2$).

Example 6

1,1'-(3-methylpentane-1,5-diyl)bis{5,5-dimethyl-3-[4-nitro-3-(trifluoromethyl)phenyl]imidazolidine-2,4-dione}

The experimental protocol used is the same as that described for the synthesis of the compound of Example 1, 1,5-dibromo-3-methylpentane replacing 1,4-dibromobutane. The expected compound is obtained in the form of a light yellow coloured foam with a yield of 39%.

$^1$H NMR 400 MHz (DMSO-d$_6$) δ: 8.30 (d, 2H, Ph); 8.20 (d, 2H, Ph); 8.07 (dd, 2H, Ph); 3.38 (m, 4H, 2×NCH$_2$); 1.72 (m, 4H, 2×CH$_2$); 1.53 (m, 1H, CH); 1.49 (s, 12H, 4×CH$_3$); 1.00 (d, 3H, CH$_3$).

Example 7

1,1'-(oxydiethane-2,1-diyl)bis{5,5-dimethyl-3-[4-nitro-3-(trifluoromethyl)-phenyl]imidazolidine-2,4-dione}

The experimental protocol used is the same as that described for the synthesis of the compound of Example 1, bis-(2-bromoethyl)ether replacing 1,4-dibromobutane. The expected compound is obtained in the form of a white solid with a yield of 70%. Melting point: 186-188° C.
$^1$H NMR 400 MHz (DMSO-d$_6$) δ: 8.28 (d, 2H, Ph); 8.16 (d, 2H, Ph); 8.03 (dd, 2H, Ph); 3.67 (t, 4H, 2×CH$_2$); 3.52 (t, 4H, 2×CH$_2$); 1.47 (s, 12H, 4×CH$_3$).

Example 8

1,1'-pentane-1,5-diylbis{3-[4-amino-3-(trifluoromethyl)phenyl]-5,5-dimethylimidazolidine-2,4-dione}

A mixture of the compound of Example 2 (410 mg, 0.58 mmole) and SnCl$_2$, 2H$_2$O (1.32 g, 5.8 mmoles) in AcOEt (10 ml) is heated at 80° C. for 90 minutes. The reaction medium is then cooled down to 0° C. before being poured into a saturated aqueous solution of Na$_2$CO$_3$ (40 ml). The heterogeneous mixture thus obtained is filtered on celite and rinsed with AcOEt (2×50 ml). After decantation, the organic phases are combined, dried over Na$_2$SO$_4$, filtered and the solvent is evaporated off under reduced pressure. The residue obtained is taken up in a mixture of heptane/AcOEt in order to produce a white solid, after filtration, with a yield of 78% (290 mg). Melting point: 108-109° C.
$^1$H NMR 400 MHz (DMSO-d$_6$) δ: 7.32 (d, 2H, Ph); 7.23 (dd, 2H, Ph); 6.85 (d, 2H, Ph); 5.80 (s, 4H, 2×NH$_2$); 3.27 (m, 4H, 2×NCH$_2$); 1.64 (m, 4H, 2×CH$_2$); 1.40 (s, 12H, 4×CH$_3$); 1.31 (m, 2H, CH$_2$).

Example 9

N,N'-(pentane-1,5-diylbis{(4,4-dimethyl-2,5-dioxoimidazolidine-3,1-diyl)[2-(trifluoromethyl)-4,1-phenylene]})diacetamide The compound of Example 8 (161 mg, 0.25 mmol) is mixed under an argon atmosphere with acetyl chloride (10 ml) and stirring is maintained for 15 hours at 23° C. The reaction mixture is then evaporated to dryness (entrainment with toluene) and the residue obtained is purified on a silica column (eluent: CH$_2$Cl$_2$/EtOH from 99/1 to 90/10). After evaporation, the expected compound is obtained in the form of a cream coloured foam with a yield of 52%.
$^1$H NMR 400 MHz (DMSO-d$_6$) δ: 9.63 (s, 2H, CONH); 7.81 (d, 2H, Ph); 7.69 (dd, 2H, Ph); 7.58 (d, 2H, Ph); 3.30 (m, 4H, 2×NCH$_2$); 2.06 (s, 6H, 2×CH$_3$); 1.67 (m, 4H, 2×CH$_2$); 1.40 (s, 12H, 4×CH$_3$); 1.40 (m, 2H, CH$_2$).

Example 10

1,1'-pentane-1,5-diylbis[5,5-dimethyl-3-(3-methyl-4-nitrophenyl)imidazolidine-2,4-dione]

10.1) 5,5-dimethyl-3-(3-methyl-4-nitrophenyl)imidazolidine-2,4-dione

A mixture of 5-fluoro-2-nitrotoluene (1.55 g, 10 mmoles), 5,5-dimethylhydantoin (1.28 g, 10 mmoles), K$_2$CO$_3$ (1.38 g, 10 mmoles) in DMF (15 ml) is introduced into a tube to be placed in a microwave oven and irradiated at 100° C. for 70 minutes, under magnetic stirring. The reaction mixture is then poured into water (200 ml) and extracted with AcOEt (2×75 ml). The organic phases are combined, washed with salt water, dried over Na$_2$SO$_4$ and filtered. The filtrate is concentrated under reduced pressure and the residue is purified by chromatography on a silica column (eluent: Heptane/AcOEt: 7/3). The expected compound is obtained in the form of a white solid with a yield of 25% (666 mg). Melting point: 177-178° C.
$^1$H NMR 400 MHz (DMSO-d$_6$) δ: 8.70 (s, 1H, NH); 8.10 (d, 1H, Ph); 7.58 (s, 1H, Ph); 7.52 (dd, 1H, Ph); 2.54 (s, 3H, CH$_3$); 1.41 (s, 6H, 2×CH$_3$).

10.2) 1,1'-pentane-1,5-diylbis[5,5-dimethyl-3-(3-methyl-4-nitrophenyl)imidazolidine-2,4-dione]

The experimental protocol used is the same as that described for the synthesis of the compound of Example 2, intermediate 10.1 replacing 5,5-dimethyl-3-[4-nitro-3-(trifluoromethyl)phenyl]-imidazolidine-2,4-dione. The expected compound is obtained in the form of a white solid with a yield of 67% (495 mg). Melting point: 130-131° C.
$^1$H NMR 400 MHz (DMSO-d$_6$) δ: 8.09 (d, 2H, Ph); 7.58 (s, 2H, Ph); 7.52 (dd, 2H, Ph); 3.32 (s, 4H, 2×NCH$_2$); 2.53 (s, 6H, 2×CH$_3$); 1.68 (m, 4H, 2×CH$_2$); 1.46 (s, 12H, 4×CH$_3$); 1.38 (m, 2H, CH$_2$).

Example 11

1,1'-pentane-1,5-diylbis{5,5-dimethyl-3-[4-nitro-2-(trifluoromethyl)phenyl]imidazolidine-2,4-dione}

11.1) 5,5-dimethyl-3-[4-nitro-2-(trifluoromethyl)phenyl]imidazolidine-2,4-dione

The experimental protocol used is the same as that described for the synthesis of intermediate 10.1, 2-fluoro-5-nitrobenzotrifluoride replacing 5-fluoro-2-nitrotoluene. The expected compound is obtained in the form of a white solid with a yield of 29%. Melting point: 175-176° C.
$^1$H NMR 400 MHz (DMSO-d$_6$) δ: 8.76 (s, 1H, NH); 8.68 (dd, 1H, Ph); 8.58 (d, 1H, Ph); 8.04 (d, 1H, Ph); 1.47 (s, 3H, CH$_3$); 1.38 (s, 3H, CH$_3$).

11.2) 1,1'-pentane-1,5-diylbis{5,5-dimethyl-3-[4-nitro-2-(trifluoromethyl)phenyl]-imidazolidine-2,4-dione}

The experimental protocol used is the same as that described for the synthesis of the compound of Example 2, intermediate 11.1 replacing 5,5-dimethyl-3-[4-nitro-3-(trifluoromethyl)phenyl]-imidazolidine-2,4-dione. The expected compound is obtained in the form of a light yellow foam with a yield of 12%.
$^1$H NMR 400 MHz (DMSO-d$_6$) δ: 8.68 (m, 2H, Ph); 8.58 (d, 2H, Ph); 8.04 (d, 2H, Ph); 3.33 (m, 4H, 2×NCH$_2$); 1.66 (m, 4H, 2×CH$_2$); 1.50 (m, 6H, 2×CH$_3$); 1.42 (m, 6H, 2×CH$_3$); 1.35 (m, 2H, CH$_2$).

Example 12

1,1'-pentane-1,5-diylbis[3-(3-chloro-4-nitrophenyl)-5,5-dimethyl-imidazolidine-2,4-dione]

12.1) 3-(3-chloro-4-nitrophenyl)-5,5-dimethylimidazolidine-2,4-dione

The experimental protocol used is the same as that described for the synthesis of intermediate 10.1, 2-chloro-4- fluoronitrobenzene replacing 5-fluoro-2-nitrotoluene. The expected compound is obtained in the form of a pale yellow solid with a yield of 28%. Melting point: 144-145° C.

$^1$H NMR 400 MHz (DMSO-d$_6$) δ: 8.77 (s, 1H, NH); 8.21 (d, 1H, Ph); 7.92 (d, 1H, Ph); 7.71 (dd, 1H, Ph); 1.41 (s, 6H, 2×CH$_3$).

12.2) 1,1'-pentane-1,5-diylbis[3-(3-chloro-4-nitrophenyl)-5,5-dimethylimidazolidine-2,4-dione]

The experimental protocol used is the same as that described for the synthesis of the compound of Example 2, intermediate 12.1 replacing 5,5-dimethyl-3-[4-nitro-3-(trifluoromethyl)-phenyl]-imidazolidine-2,4-dione. The expected compound is obtained in the form of a light yellow foam with a yield of 7%.

$^1$H NMR 400 MHz (DMSO-d$_6$) δ: 8.28 (d, 2H, Ph); 7.99 (d, 2H, Ph); 7.79 (dd, 2H, Ph); 3.37 (m, 4H, 2×NCH$_2$); 1.74 (m, 4H, 2×CH$_2$); 1.53 (m, 12H, 4×CH$_3$); 1.46 (m, 2H, CH$_2$).

Example 13

1,1'-pentane-1,5-diylbis[3-(3-methoxy-4-nitrophenyl)-5,5-dimethyl-imidazolidine-2,4-dione]

13.1) 3-(3-methoxy-4-nitrophenyl)-5,5-dimethylimidazolidine-2,4-dione

The experimental protocol used is the same as that described for the synthesis of intermediate 10.1, 5-fluoro-2-nitroanisole replacing 5-fluoro-2-nitrotoluene. The expected compound is obtained in the form of a white solid with a yield of 20%.

$^1$H NMR 400 MHz (DMSO-d$_6$) δ: 8.70 (s, 1H, NH); 7.99 (d, 1H, Ph); 7.47 (d, 1H, Ph); 7.20 (dd, 1H, Ph); 3.91 (s, 3H, OCH$_3$); 1.42 (s, 6H, 2×CH$_3$).

13.2) 1,1'-pentane-1,5-diylbis[3-(3-methoxy-4-nitrophenyl)-5,5-dimethyl-imidazolidine-2,4-dione]

The experimental protocol used is the same as that described for the synthesis of the compound of Example 2, intermediate 13.1 replacing 5,5-dimethyl-3-[4-nitro-3-(trifluoromethyl)phenyl]-imidazolidine-2,4-dione. The expected compound is obtained in the form of a white foam with a yield of 10%.

$^1$H NMR 400 MHz (DMSO-d$_6$) δ: 8.07 (d, 2H, Ph); 7.54 (d, 2H, Ph); 7.28 (dd, 2H, Ph); 3.97 (s, 6H, 2×OCH$_3$); 3.38 (m, 4H, 2×NCH$_2$); 1.74 (m, 4H, 2×CH$_2$); 1.53 (m, 12H, 4×CH$_3$); 1.46 (m, 2H, CH$_2$).

Example 14 dimethyl{pentane-1,5-diylbis[(4,4-dimethyl-2,5-dioxoimidazolidine-3,1-diyl)(2-methyl-4,1-phenylene)]}biscarbamate

14.1) 1,1'-pentane-1,5-diylbis[3-(4-amino-3-methylphenyl)-5,5-dimethyl-imidazolidine-2,4-dione]

The experimental protocol used is the same as that described for the synthesis of the compound of Example 8 starting from the compound of Example 10, which replaces the compound of Example 2. The expected compound is obtained in the form of a white foam with a yield of 69%.

$^1$H NMR 400 MHz (DMSO-d$_6$) δ: 6.79 (m, 4H, Ph); 6.60 (d, 2H, Ph); 5.02 (s, 4H, 2×NH$_2$); 3.26 (m, 4H, 2×NCH$_2$); 2.03 (s, 6H, 2×CH$_3$); 1.62 (m, 4H, 2×CH$_2$); 1.39 (s, 12H, 4×CH$_3$); 1.31 (m, 2H, CH$_2$).

14.2) dimethyl {pentane-1,5-diylbis[(4,4-dimethyl-2,5-dioxoimidazolidine-3,1-diyl)(2-methyl-4,1-phenylene)]}biscarbamate Intermediate 14.1 (268 mg, 0.5 mmole) dissolved in anhydrous pyridine (10 ml) is mixed with methyl chloroformate (0.8 ml, 10 mmoles) under an argon atmosphere. Stirring is maintained for 18 hours at 90° C. The reaction mixture is then poured into ice water and extracted using AcOEt (2×50 ml). The organic phases are combined and washed with salt water (25 ml). The organic solution is dried over Na$_2$SO$_4$, filtered and the solvent is evaporated off under reduced pressure. The residue is purified on a silica column (eluent: Heptane/AcOEt: 4/6 to 0/1). The expected compound is obtained in the form of a white foam with a yield of 40% (130 mg).

$^1$H NMR 400 MHz (DMSO-d$_6$) δ: 8.92 (s, 2H, NH); 7.43 (d, 2H, Ph); 7.17 (d, 2H, Ph); 7.12 (dd, 2H, Ph); 3.66 (s, 6H, 2×OCH$_3$); 3.29 (m, 4H, 2×NCH$_2$); 2.20 (s, 6H, 2×CH$_3$); 1.66 (m, 4H, 2×CH$_2$); 1.42 (s, 12H, 4×CH$_3$); 1.37 (m, 2H, CH$_2$).

Example 15

4,4'-[pentane-1,5-diylbis(4,4-dimethyl-2,5-dioxoimidazolidine-3,1-diyl)]bis(2-methylbenzonitrile)

15.1) 4-(4,4-dimethyl-2,5-dioxoimidazolidin-1-yl)-2-methylbenzonitrile

The experimental protocol used is the same as that described for the synthesis of intermediate 5.1, 4-fluoro-2-methylbenzonitrile replacing 4-fluoro-2-(trifluoromethyl)benzonitrile. After recrystallization from EtOH (75 ml), the expected compound is obtained in the form of a white solid with a yield of 5%.

$^1$H NMR 400 MHz (DMSO-d$_6$) δ: 8.70 (s, 1H, NH); 7.89 (d, 1H, Ph); 7.54 (s, 1H, Ph); 7.43 (d, 1H, Ph); 2.49 (s, 3H, CH$_3$); 1.40 (s, 6H, 2×CH$_3$).

15.2) 4,4'-[pentane-1,5-diylbis(4,4-dimethyl-2,5-dioxoimidazolidine-3,1-diyl)]bis(2-methylbenzonitrile)

The experimental protocol used is the same as that described for the synthesis of the compound of Example 2, intermediate 15.1 replacing 5,5-dimethyl-3-[4-nitro-3-(trifluoromethyl)phenyl]-imidazolidine-2,4-dione. The expected compound is obtained in the form of a white solid with a yield of 66%. Melting point: 148-149° C.

$^1$H NMR 400 MHz (DMSO-d$_6$) δ: 7.81 (d, 2H, Ph); 7.49 (d, 2H, Ph); 7.39 (dd, 2H, Ph); 3.30 (m, 4H, 2×NCH$_2$); 2.43 (s, 6H, 2×CH$_3$); 1.62 (m, 4H, 2×CH$_2$); 1.39 (s, 12H, 4×CH$_3$); 1.31 (m, 2H, CH$_2$).

Example 16

4,4'-[pentane-1,5-diylbis(4,4-dimethyl-2,5-dioxoimidazolidine-3,1-diyl)]bis(2-chlorobenzonitrile)

16.1) 2-chloro-4-(4,4-dimethyl-2,5-dioxoimidazolidin-1-yl)benzonitrile

The experimental protocol used is the same as that described for intermediate 5.1, 2-chloro-4-fluorobenzonitrile replacing 4-fluoro-2-(trifluoromethyl)benzonitrile. The expected compound is obtained in the form of a white solid with a yield of 23%.

$^1$H NMR 400 MHz (DMSO-$d_6$) δ: 8.76 (s, 1H, NH); 8.08 (d, 1H, Ph); 7.90 (d, 1H, Ph); 7.67 (dd, 1H, Ph); 1.40 (s, 6H, 2×CH$_3$).

16.2) 4,4'-[pentane-1,5-diylbis(4,4-dimethyl-2,5-dioxoimidazolidine-3,1-diyl)]bis(2-chlorobenzonitrile)

The experimental protocol used is the same as that described for the synthesis of the compound of Example 2, intermediate 16.1 replacing 5,5-dimethyl-3-[4-nitro-3-(trifluoromethyl)phenyl]-imidazolidine-2,4-dione. The expected compound is obtained in the form of a white solid with a yield of 51%. Melting point: 166-167° C.

$^1$H NMR 400 MHz (DMSO-$d_6$) δ: 8.08 (d, 2H, Ph); 7.90 (d, 2H, Ph); 7.68 (dd, 2H, Ph); 3.30 (m, 4H, 2×NCH$_2$); 1.64 (m, 4H, 2×CH$_2$); 1.45 (s, 12H, 4×CH$_3$); 1.38 (m, 2H, CH$_2$).

Example 17

1,1'-propane-1,3-diylbis{5,5-dimethyl-3-[4-nitro-3-(trifluoromethyl)-phenyl]imidazolidine-2,4-dione}

The experimental protocol used is the same as that described for the synthesis of the compound of Example 1, 1,3-diiodopropane replacing 1,4-dibromobutane. The expected compound is obtained in the form of a white solid with a yield of 15% (50 mg). Melting point: 164-165° C.

$^1$H NMR 400 MHz (DMSO-$d_6$) δ: 8.33 (d, 2H, Ph); 8.21 (d, 2H, Ph); 8.09 (dd, 2H, Ph); 3.45 (t, 4H, 2×NCH$_2$); 2.01 (m, 2H, CH$_2$); 1.50 (s, 12H, 4×CH$_3$).

Example 18

2-{5,5-dimethyl-3-[4-nitro-3-(trifluoromethyl)phenyl]-2,4-dioxoimidazolidin-1-yl}-N-(2-{5,5-dimethyl-3-[4-nitro-3-(trifluoromethyl)-phenyl]-2,4-dioxoimidazolidin-1-yl}ethyl)-N-methylethanaminium chloride The experimental protocol used is the same as that described for the synthesis of the compound of Example 1, mechlorethamine hydrochloride replacing 1,4-dibromobutane. The expected compound is obtained in the form of a light yellow coloured solid with a yield of 30%. Melting point: 136-137° C.

$^1$H NMR 400 MHz (DMSO-$d_6$) δ: 11.08 (broad s, 1H, NH$^+$); 8.31 (m, 4H, Ph); 8.10 (d, 2H, Ph); 3.87 (m, 4H, 2×NCH$_2$); 3.51 (m, 2H, NCH$_2$); 3.38 (m, 2H, NCH$_2$); 2.99 (broad s, 3H, CH$_3$); 1.55 (s, 12H, 4×CH$_3$).

Example 19

1,1'-(2Z)-but-2-ene-1,4-diylbis{5,5-dimethyl-3-[4-nitro-3-(trifluoromethyl)phenyl]imidazolidine-2,4-dione}

The experimental protocol used is the same as that described for the synthesis of the compound of Example 1, cis-1,4-dichloro-2-butene replacing 1.4 dibromobutane. The expected compound is obtained in the form of a pale yellow solid with a yield of 40%. Melting point: 191-193° C.

$^1$H NMR 400 MHz (DMSO-$d_6$) δ: 8.34 (d, 2H, Ph); 8.22 (d, 2H, Ph); 8.09 (dd, 2H, Ph); 5.61 (q, 2H, CH═CH); 4.2 (q, 4H, 2×CH$_2$); 1.50 (s, 12H, 4×CH$_3$).

Example 20

4,4'-[pentane-1,5-diylbis(5,7-dioxo-4,6-diazaspiro[2.4]heptane-4,6-diyl)]bis[2-(trifluoromethyl)benzonitrile]

20.1) 1-({[4-cyano-3-(trifluoromethyl)phenyl]carbamoyl}amino)cyclopropanecarboxylic acid A solution of 4-isocyanato-2-(trifluoromethyl)benzonitrile (4.56 g, 21.5 mmol) in acetone (12 ml) is added dropwise to 1-aminocyclopropane carboxylic acid (2.02 g, 20 mmol) dissolved in an aqueous solution of sodium hydroxide (12 ml, 0.8 g, 20 mmol). The reaction medium is stirred for 1 hour at ambient temperature then poured into an aqueous solution of sodium hydroxide (1N, 40 ml). The solution obtained is washed with ethyl acetate (30 ml) then acidified by the addition of an aqueous solution of sulphuric acid (2M, 30 ml) and extracted with ethyl acetate (2×50 ml). The organic phase thus obtained is washed with water then with a saturated aqueous solution of sodium chloride, dried over Na$_2$SO$_4$ and filtered. The solvent is evaporated off under reduced pressure. The residue obtained is taken up in ethyl ether in order to produce a white solid, after filtration, with a yield of 50% (3.16 g).

20.2) 4-(5,7-dioxo-4,6-diazaspiro[2.4]hept-6-yl)-2-(trifluoromethyl)benzonitrile Oxalyl chloride (1.12 ml, 13 mmol) is added under argon to a solution of intermediate 20.1 (3.16 g, 10 mmol) and DMF (0.5 ml) in 1,4-dioxane (20 ml). The reaction medium is stirred under reflux for an hour and the solvent is evaporated off under reduced pressure. The residue is taken up in water (30 ml) and the solution obtained is extracted with ethyl acetate (50 ml). The organic phase is successively washed with water and with a saturated solution of sodium chloride and dried over Na$_2$SO$_4$. The solvent is evaporated off under reduced pressure. The residue obtained is taken up in ethyl ether in order to produce a white solid, after filtration, with a yield of 20% (0.6 g).

$^1$H NMR 400 MHz (DMSO-$d_6$) δ: 8.91 (s, 1H, NH); 8.27 (d, 1H, Ph); 8.18 (s, 1H, Ph); 8.04 (d, 1H, Ph); 1.3-1.45 (m, 4H, 2×CH$_2$ spiro).

20.3) 4,4'-[pentane-1,5-diylbis(5,7-dioxo-4,6-diazaspiro[2.4]heptane-4,6-diyl)]bis[2-(trifluoromethyl)benzonitrile]

The experimental protocol used is the same as that described for the synthesis of the compound of Example 2, intermediate 20.2 replacing 5,5-dimethyl-3-[4-nitro-3-(trifluoromethyl)-phenyl]-imidazolidine-2,4-dione. The expected compound is obtained in the form of a white solid. Melting point: 154-155° C.

$^1$H NMR 400 MHz (DMSO-$d_6$) δ: 8.27 (d, 2H, Ph); 8.17 (d, 2H, Ph); 8.03 (dd, 2H, Ph); 3.14 (t, 4H, CH$_2$×2); 1.64 (m, 4H, 2×CH$_2$); 1.55 (m, 4H, 2×CH$_2$ spiro); 1.36 (m, 6H, CH$_2$ central, 2×CH$_2$ spiro).

Example 21

4,4'-[(2Z)-but-2-ene-1,4-diylbis(4,4-dimethyl-2,5-dioxoimidazolidine-3,1-diyl)]bis[2-(trifluoromethyl)benzonitrile]

The experimental protocol used is the same as that described for the synthesis of Example 1, cis-1,4-dichloro-2-butene replacing 1.4 dibromobutane and intermediate 5.1 replacing 5,5-dimethyl-3-[4-nitro-3-(trifluoromethyl)-phenyl]-imidazolidine-2,4-dione. The expected compound is obtained in the form of a light beige solid. Melting point: 188-190° C.

$^1$H NMR 400 MHz (DMSO-$d_6$) δ: 8.32 (d, 2H, Ph); 8.19 (d, 2H, Ph); 8.05 (dd, 2H, Ph); 5.60 (q, 2H, CH═CH); 4.2 (q, 4H, 2×$CH_2$); 1.49 (s, 12H, 4×$CH_3$).

Example 22

4,4'-{(2R,3S)-oxirane-2,3-diylbis[methanediyl(4,4-dimethyl-2,5-dioxoimidazolidine-3,1-diyl)]}bis[2-(trifluoromethyl)benzonitrile]

The compound of Example 21 (90 mg, 0.139 mmol) is mixed under argon with 3-metachloroperbenzoic acid (72.5 mg, 0.210 mmol) in anhydrous dichloromethane (10 ml). The mixture is stirred at ambient temperature. The progression of the reaction is monitored by TLC (eluent DCM/EtOH: 95/05). After 4 days, starting compound remains. A fresh quantity of metachloroperbenzoic acid (0.124 g, 0.36 mmol) is added to the reaction medium and the reaction medium is stirred at ambient temperature for another 4 days. The solvent is evaporated off under reduced pressure and the residue is purified by flash chromatography (BIOTAGE 25+M column, gradient dichloromethane/acetone: 0% to 8% of acetone). The expected compound is obtained in the form of a white solid, with a yield of 50%. Melting point: 108-110° C.

$^1$H NMR 400 MHz (DMSO-$d_6$) δ: 8.32 (d, 2H, Ph); 8.21 (d, 2H, Ph); 8.05 (dd, 2H, Ph); 4.05 (q, 2H, CH—CH); 3.28 (m, 4H, 2×$CH_2$); 1.53 (d, 12H, 4×$CH_3$).

Example 23

4,4'-{(1R,2R)-cyclopropane-1,2-diylbis[methanediyl(4,4-dimethyl-2,5-dioxoimidazolidine-3,1-diyl)]}bis[2-(trifluoromethyl)benzonitrile]

The experimental protocol used is the same as that described for the synthesis of the compound of Example 1, trans-1,2-bis(bromomethyl)cyclopropane (prepared according to *J. Med. Chem.* 2003, 46 (21), 4586-4600) replacing 1,4-dibromobutane. The expected compound is obtained in the form of a cream coloured solid. Melting point: 178-180° C.

$^1$H NMR 400 MHz (DMSO-$d_6$) δ: 8.26 (d, 2H, Ph); 8.15 (d, 2H, Ph); 8.01 (dd, 2H, Ph); 3.2-3.4 (m, 4H, 2×$NCH_2$); 2.49 (s, 12H, 4×$CH_3$); 1.24 (m, 2H, 2×CH); 0.61 (t, 2H, 1×$CH_2$).

Pharmacological Study of the Compounds According to the Invention
Measurements of Anti-Proliferative Activities:
1. Anti-Proliferative Activity on LNCaP in Complete Medium The anti-proliferative activity of the compounds of the present invention is determined on LNCaP in complete medium by applying the following experimental procedure:

The LNCaP cell type (ATCC, 1740) originates from a prostate carcinoma expressing the androgen receptor, this line is hormone-dependent.

Maintenance of the LNCaP line is carried out in complete culture medium: RPMI, 10% of foetal calf serum, 2 mM glutamine, 100 U/ml penicillin, 0.1 mg/ml of streptomycin and 0.01M HEPES, 1 mM sodium pyruvate, 40% of D-glucose.

Seeding the plates:
The LNCaP line is seeded at 20,000 cells/well in 90 μA of complete medium in 96-well plates coated with poly-D-lysine (Biocoat, Costar).

Treatment of the cells: 24 h after the seeding, the cells are treated with 10 μl/well of compound diluted in the culture medium. The concentrations used are the following: 1 nM/10/30/100/300/1000/3000/10,000/100,000 nM. The cells are incubated for 144 h at 37° C., 5% $CO_2$.

Reading: After incubation for 6 days, 10 μL of the "WST-1 cell proliferation" reagent (Roche ref 1644807) is added to each well. After incubation for 2 hours at 37° C., 5% $CO_2$, the absorbance at 450 nm is measured by spectrophotometry (Envision, Perkin Elmer).

Results: The experiments are carried out in duplicate and the best compounds are tested twice. A concentration value inhibiting the cell proliferation by 50% ($IC_{50}$) is calculated.

All the compounds of Examples 1 to 23 described previously have an $IC_{50}$ of less than or equal to 5000 nM on the LNCaP cells in culture.

Among those, the compounds of the following examples have an $IC_{50}$ of less than 1500 nM on the LNCaP cells in culture: 1, 2, 4, 7, 10, 13, 14, 15, 16, 19, 20, 21 and 22.

The compounds of the following examples have an $IC_{50}$ of less than 500 nM on the LNCaP cells in culture: 1, 2, 7, 15, 19, 20, 21 and 22.

2. Antiproliferative Activity on LNCaP in a Medium Depleted in Steroids:

The pro- and/or anti-proliferative activity of the compounds of the present invention is determined on LNCaP in medium depleted in steroids.

The LNCaP (ATCC, 1740) line originates from a carcinoma of the prostate expressing the androgen receptor, it is hormone-dependent.

The maintenance of the LNCaP line is carried out under the usual conditions in RPMI, 10% of foetal calf serum, 2 mM of glutamine, 100 U/ml of penicillin, 0.1 mg/ml of streptomycin and 0.01M HEPES, 1 mM sodium pyruvate, 40% of D-glucose.

For the study under conditions without steroids, 24 hours before the seeding the culture medium of the cells is eliminated. The cells are washed with PBS, then incubated in the presence of RPMI medium without phenol red, 10% of foetal calf serum without steroids (treatment with carbon-dextran beforehand), 2 mM of glutamine, 100 U/ml of penicillin, 0.1 mg/ml of streptomycin and 0.01M HEPES, 1 mM of sodium pyruvate, 40% of D-glucose.

Seeding the plates:
The LNCaP line is seeded at 20,000 cells/well in 90 μl of RPMI medium with 10% foetal calf serum depleted in steroids in 96-well plates coated with poly-D-lysine (Biocoat, Costar).

Treatment of the cells: 24 h after seeding, the cells are treated with 10 μl/well of compound diluted in the culture medium. The concentrations used are the following: 1 nM/10/30/100/300/1000/3000/10,000/100,000 nM. The cells are incubated for 144 h at 37° C., 5% $CO_2$.

Reading: After incubation for 6 days, 10 μL of cell proliferation reagent WST-1 (Roche ref 1644807) is added to each well. After incubation for 2 to 4 hours at 37° C., 5% $CO_2$, the absorbance at 450 nm is measured by spectrophotometry (Envision, Perkin Elmer).

Results: The experiments are carried out in duplicate and the best compounds are tested twice. A concentration value inhibiting cell proliferation by 50% ($IC_{50}$) is calculated.

As described previously (Veldscholte J, Berrevoets C A, Brinkmann A O, Grootegoed J A, Mulder E. Biochemistry 1992 Mar. 3; 31(8):2393-9), nilutamide presents an agonist activity at low concentrations, then an inhibitory activity at high concentrations.

Surprisingly, compounds 1 to 23 do not have an agonist effect on the LNCaP cultured in a medium depleted in steroids. Moreover, compounds 2 and 19 show a visible inhibitory activity at low concentrations.

Figure 1:
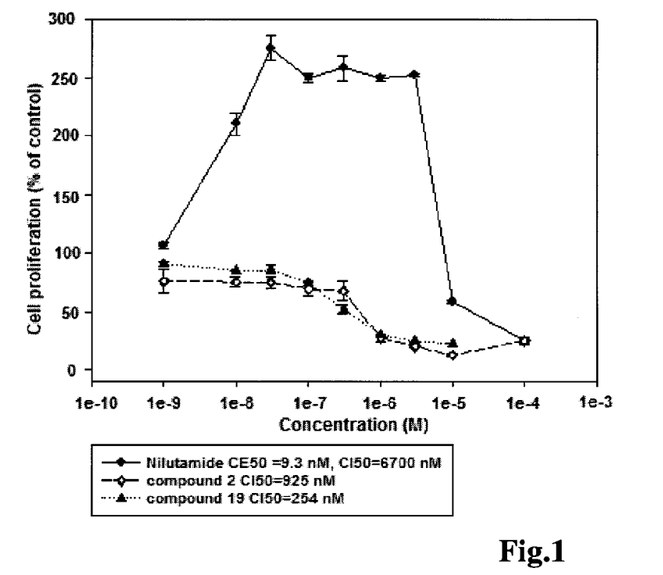
FIG. 1 represents the effect of the compounds of Examples 2 and 19 on the proliferation of LNCaP cells cultured in medium without steroids.
Figure 2:
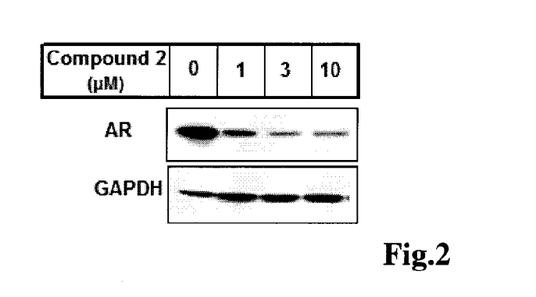
FIGS. 2 to 9 represent the effects of the compounds of Examples 2, 7, 10, 15, 16, 19, 21, and 22 on the reduction in protein expression of the androgen receptor.
Figure 3:
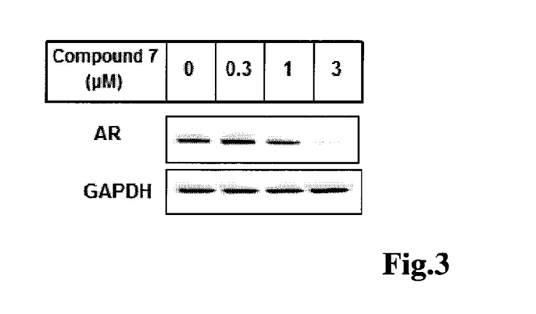
Figure 4:
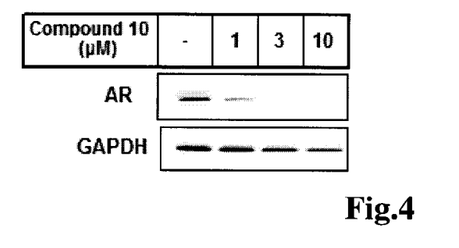
Figure 5:
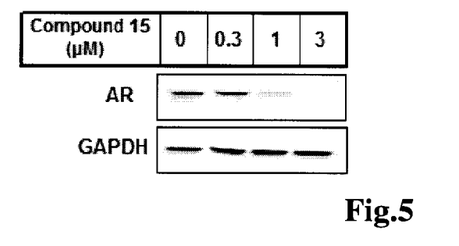
Figure 6:
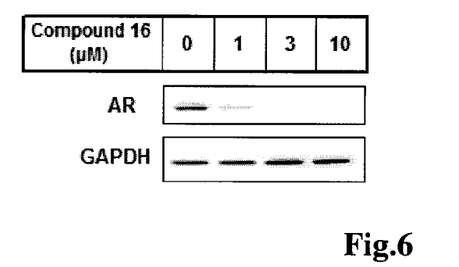
Figure 7:
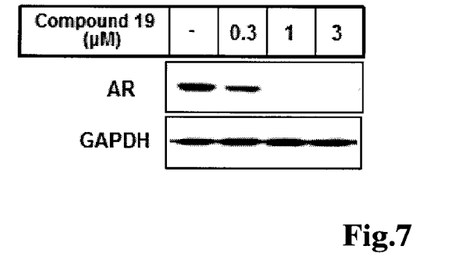
Figure 8:
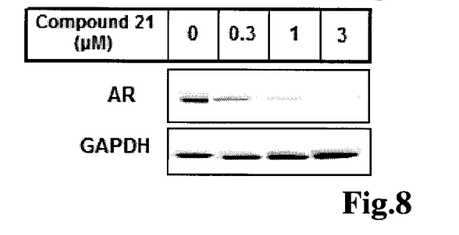
Figure 9:
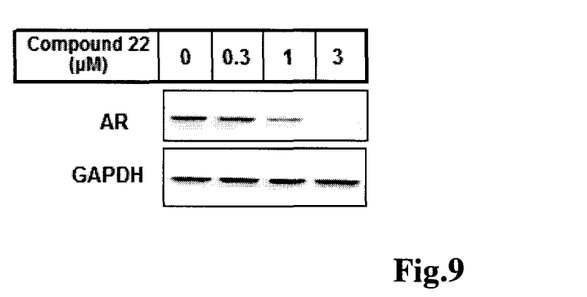

The effect of compounds 2 and 19 on the cell proliferation of the LNCaP cultured in medium depleted in steroids is shown in FIG. 1.

3. Measurement of Protein Expression of the Androgen Receptor

The cells of the LNCaP line are seeded at a rate of 2.5 millions of cells per 10 cm Petri dish in RPMI, 10% of foetal calf serum, 2 mM of glutamine, 100 U/ml of penicillin, 0.1 mg/ml of streptomycin and 0.01M HEPES, 1 mM of sodium pyruvate, 40% of D-glucose. 4 days later, the cells are treated with the compound to be tested. 72 hours after the treatment the cells are lyzed in lysis buffer (50 mM Tris pH 7.4, 150 mM NaCl, 1 mM EDTA, 20 mM NaF, 100 mM $Na_2VO_3$, 0.5% of NP40, 1% of Triton X-100, 1 mM EGTA, Pefabloc, protease inhibitor cocktail 11836170001 RocheDiagnostics, Phosphatase inhibitor cocktail set II Calbiochem). The cells are then scrapped and the lysate transferred into QIAshredder tubes (cat No. 79656 Qiagen) for centrifugation at 13,000 rpm for 15 min at 4° C. The supernatant is transferred into QIAshredder tubes for a second centrifugation at 13,000 rpm for 5 min in order to completely eliminate the DNA filaments. The protein concentration is then determined (Bio-Rad DC protein assay kit) and adjusted so as to load the same quantity of proteins per well (10 and 20 per well depending on the experiments). The loading buffer (sample loading buffer 3×ref 7722 Cell signaling technology) with added 1% beta-mercaptoethanol and 50 mM DTT, is added to the samples which are then heated for 10 min at 90° C. The samples are deposited under a volume of 20 μl on NuPAGE 4-12% Bis-Tris gels (cat No. NP0322BOX, Invitrogen). The migration takes place in MOPS buffer (Invitrogen) and is carried out for 1 hour at 180V. The proteins are transferred onto a nitrocellulose membrane (Hybond ECL RPN78D, GE Healthcare) under semi-dry conditions, in the presence of transfer buffer (NP0006-1, Invitrogen) over 45 min at 15V. The membrane is then blocked for 1 hour in blocking buffer (Non-fat dry milk, cat 170-6404, Biorad) at 5% in Tris Buffer saline (TBS) 0.1% Tween 20. Then it is incubated at 4° C. overnight in the presence of primary antibody directed against the androgen receptor (AR441, sc-7305, Santa Cruz) diluted to $1/2000^{th}$ in blocking buffer as well as in the presence of primary antibody directed against GAPDH (Cat.MAB374, Millipore) diluted to $1/20,000^{th}$ in blocking buffer (monitoring of protein load). The membrane is then washed 3 times in washing buffer (TBS, 0.1% Tween 20). The membrane is then incubated in the presence of secondary anti-immunoglobulin mouse antibody coupled with HRP (Goat anti-mouse IgG-HRP, sc 2031, Santa Cruz) diluted to $1/5000^{th}$ in blocking buffer. The membrane is then washed 3 times in washing buffer. The proteins are revealed by electrochemiluminescence (western Blotting detection system ECL+, Amersham), being detected either by using photographic films (Biomax light, Sigma), or by a chemiluminescence acquisition system (G:Box, Syngene)

Figure 10:
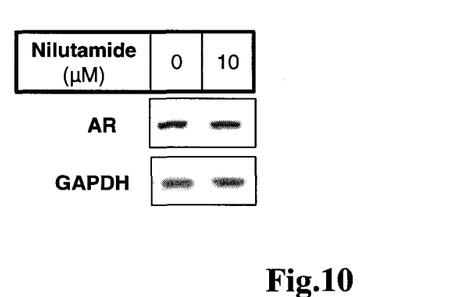
FIG. 10 represents the effect of nilutamide on the reduction in protein expression of the androgen receptor.

The effects of compounds 2, 7, 10, 15, 16, 19, 21, 22 are shown in FIGS. 2 to 9: these compounds reduce protein expression of the androgen receptor. On the other hand, as FIG. 10 shows, nilutamide does not reduce protein expression of this receptor (FIG. 10).

The invention claimed is:

1. A compound of formula (I)

wherein:
$R^1$ represents a cyano, nitro, amino, —$NHCOOR^4$ or —$NHCOR^4$ radical;
$R^2$ represents a halo, alkyl, haloalkyl, or alkoxy radical;
$R^3$ represents an alkyl radical or a hydrogen atom; or the two $R^3$ radicals form together with the carbon atom to which they are attached a cycloalkyl comprising 3 to 4 members;
X represents
either a linear or branched alkylene chain with 3 to 7 carbon atoms, wherein the chain comprises one or more additional identical or different members chosen from —O—, —N($R^5$)—, —S—, —SO— or —$SO_2$—;
or a group,
wherein $n_1$ and $p_1$ are two integers, the sum of $n_1+p_1$ is an integer chosen from 2, 3, 4 or 5;
$R^6$ and $R^7$ form together a covalent bond, or $R^6$ and $R^7$ form together with the carbon atoms to which they are connected a ring or a cycloalkyl comprising 3 to 6 members;
$R^4$ represents an alkyl, aryl, or heteroaryl radical;
$R^5$ represents a hydrogen, an alkyl, or aralkyl radical;
or a pharmaceutically acceptable salt thereof.

2. The compound according to claim 1, wherein X represents a linear or branched alkylene chain with 3 to 7 carbon atoms, wherein said chain comprises one or more additional identical or different members chosen from —O—, —($R^5$)—, —S—, —SO—, or —$SO_2$—; or a pharmaceutically acceptable salt thereof.

3. The compound according to claim 1, wherein X represents an alkylene chain comprising a single member chosen from —O—, —N(R$^5$)—, —S—, —SO—, or —SO$_2$—; or a pharmaceutically acceptable salt thereof.

4. The compound according to claim 1, wherein X represents a group,
wherein n$_1$ and p$_1$ are each integers, and the sum n$_1$+p$_1$ is an integer chosen from 2, 3, 4 or 5;
R$^6$ and R$^7$ form together a covalent bond, or R$^6$ and R$^7$ form together with the carbon atoms to which they are connected a ring or a cycloalkyl comprising 3 to 4 members;
or a pharmaceutically acceptable salt thereof.

5. The compound according to claim 4, wherein n$_1$ and p$_1$ are equal.

6. The compound according to claim 1, wherein X represents a group, and X' represents an —O—, —N(R$^5$)—, —S—, —SO—, —SO$_2$—, —(CH$_2$)— or group, and n$_2$ and p$_2$ are integers the sum of which n$_2$+p$_2$ is an integer chosen from 3, 4, 5, 6, or 7 when X' represents an —O—, —N(R$^5$)—, or —S—, —SO—, —SO$_2$— group or an integer chosen from 2, 3, 4 or 5 when X' represents a or —(CH$_2$)— group.

7. The compound according to claim 6, in which X' represents a group.

8. The compound according to claim 6, in which X' represents an —O—, —N(R$^5$)—, or —(CH$_2$)— group.

9. The compound according to claim 6, wherein n$_2$ and p$_2$ are equal.

10. The compound according to claim 1, wherein R$^3$ represents an alkyl radical or the two R$^3$ radicals form together with the carbon atom to which they are attached a cycloalkyl comprising 3 to 4 members.

11. The compound according to claim 1, wherein R$^4$ represents an alkyl radical.

12. The compound according to claim 1, wherein R$^5$ represents an alkyl radical.

13. The compound according to claim 1, wherein R$^1$ is in para position.

14. The compound according to claim 1, wherein R$^1$ is in meta position.

15. The compound according to claim 1, wherein R$^6$ and R$^7$ form together a covalent bond.

16. The compound according to claim 1, wherein R$^6$ and R$^7$ form together with the carbon atoms to which they are connected the ring.

17. The compound according to claim 1, wherein R$^6$ and R$^7$ form together with the carbon atoms to which they are connected a cycloalkyl comprising 3 to 6 members.

18. The compound according to claim 1, wherein the alkyl radical represents a methyl group.

19. A compound of formula (I) according to claim 1, chosen from:
1,1'-butane-1,4-diylbis{5,5-dimethyl-3-[4-nitro-3-(trifluoromethyl)-phenyl]imidazolidine-2,4-dione};
1,1'-pentane-1,5-diylbis{5,5-dimethyl-3-[4-nitro-3-(trifluoromethyl)-phenyl]imidazolidine-2,4-dione};
1,1'-(oxydiethane-2,1-diyl)bis{5,5-dimethyl-3-[4-nitro-3-(trifluoromethyl)-phenyl]imidazolidine-2,4-dione};
4,4'-[pentane-1,5-diylbis(4,4-dimethyl-2,5-dioxoimidazolidine-3,1-diyl)]bis(2-methylbenzonitrile);
1,1'-(2Z)-but-2-ene-1,4-diylbis{5,5-dimethyl-3-[4-nitro-3-(trifluoromethyl)phenyl]imidazolidine-2,4-dione};
and
combinations thereof;
or a pharmaceutically acceptable salt thereof.

20. A compound of the formula (I), according to claim 1, wherein the compound is 1,1'-pentane-1,5-diylbis{5,5-dimethyl-3-[4-nitro-3-(trifluoromethyl)-phenyl]imidazolidine-2,4-dione} or 1,1'-(2Z)-but-2-ene-1,4-diylbis{5,5-dimethyl-3-[4-nitro-3-(trifluoromethyl)phenyl]imidazolidine-2,4-dione} or a pharmaceutically acceptable salt thereof.

21. A method of preparing the compound according to claim 1, comprising the steps of
(i) condensing two equivalents of the arylhydantoins of general formula (II)

(II)

in the presence of a strong base, wherein R$^1$ is a nitro or cyano group, with a derivative of general formula Gp$^1$-X-Gp$^2$,
wherein Gp$^1$ and Gp$^2$ are leaving groups in the presence of a strong base,
in order to form the compound of general formula (I)

(I)

wherein and R¹ is a nitro or cyano group;

wherein, if R¹ is a nitro group, the method optionally further comprises a step of:

(ii) reducing the nitro group in order to obtain a compound of formula (III)

(III)

wherein the method optionally further comprises a step comprising:

(iii) reacting a compound of formula (III) obtained in stage (ii) with an acid chloride of general formula R⁴—COCl, in order to form a compound of formula (IV)

(IV)

(iv) reacting a compound of formula (III) obtained in stage (ii) with a chloroformate of general formula R⁴—O—CO—Cl, in order to form a compound of formula (V)

(V)

or if X in formula (I) represents a group where R⁶ and R⁷ form together a covalent bond, the method optionally further comprises a step of:

(v) oxidizing the compound of formula (I), wherein R⁶ and R⁷ form together a covalent bond, the double bond formed by R⁶ and R⁷ of the compound of formula (I) in order to obtain a compound of formula (VI)

(VI)

22. A pharmaceutical composition comprising as an active ingredient, at least one compound of claim 1, and a pharmaceutically acceptable excipient.

23. A method of treating prostate cancer comprising administering a therapeutically effective amount of a compound according to claim 22.

* * * * *